United States Patent [19]

Marion et al.

[11] 4,035,410

[45] July 12, 1977

[54] CATALYSTS AND PROCESSES FOR THE PREPARATION OF UNSATURATED NITRILES

[75] Inventors: Jacques Marion; Christian Pralus, both of Lyon, France

[73] Assignee: Produits Chimiques Ugine Kuhlmann, Paris, France

[21] Appl. No.: 561,700

[22] Filed: Mar. 25, 1975

[30] Foreign Application Priority Data

Mar. 28, 1974 France .......................... 74.10754

[51] Int. Cl.² .................................. C07C 120/14
[52] U.S. Cl. .......................... 260/465.3; 252/461; 252/462; 252/464; 252/469; 252/471; 252/472; 252/473; 252/475; 252/476; 252/456
[58] Field of Search ............................. 260/465.3

[56] References Cited
U.S. PATENT DOCUMENTS

| 3,627,817 | 12/1971 | Barnett et al. | 260/465.3 |
|---|---|---|---|
| 3,847,965 | 11/1974 | Gasson et al. | 260/465.3 |
| 3,914,278 | 10/1975 | Gasson et al. | 260/465.3 |

OTHER PUBLICATIONS

ACRYLONITRILE, Progress in Materials Science Series, vol. VI, Dalin et al., 1971, pp. 70–91.

Primary Examiner—Joseph Paul Brust
Attorney, Agent, or Firm—Brooks, Haidt, Haffner & Delahunty

[57] ABSTRACT

Catalysts for the preparation of unsaturated nitriles by the ammoxidation of olefins, such catalysts being oxides of antimony and of tin together with one or more polyvalent metal oxides and one or more monovalent metal compositions of the general formula $$Sb_a Sn_b (Me_c)_m (A_d)_n O_e \qquad (1)$$

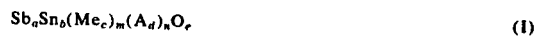

wherein Me represents a polyvalent metal and A a monovalent metal; $a$ is from one to ten, $b$ is from one to ten, $c$ is from 0.01 to five, and $d$ is from 0.01 to five; $m$ and $n$ are integers equal to or greater than one; and $e$ is the number of oxygen atoms combined with the metallic elements, together with processes for preparing nitriles by ammoxidation of olefins, especially acrylonitrile from propylene, utilizing such ammoxidation catalysts.

6 Claims, No Drawings

CATALYSTS AND PROCESSES FOR THE PREPARATION OF UNSATURATED NITRILES

BACKGROUND OF THE INVENTION

The present invention relates to the preparation of unsaturated nitriles utilizing olefin starting materials, and more particularly, to the vapor phase ammoxidation of propylene or of isobutene, respectively, to produce acrylonitrile or methacrylonitrile in the presence of catalysts having a base of antimony and of tin.

There are a number of patents, particularly French Pat. Nos. 1,299,139 and 1,293,088, which show catalysts based on the oxides of antimony and on the oxides of tin. Such catalysts enable the preparation of unsaturated nitriles starting with olefins. It has also been shown in other patents, particularly in Certificate of Addition 81,246 to French Pat. No. 1,299,139 and in French Pat. Nos. 2,176,770 and 2,176,139 that the oxides of polyvalent metals such as iron, copper, vanadium, titanium, calcium, and barium are able to be advantageously used in combination with the oxides of antimony and of tin to oxidize propylene in the presence of ammonia to obtain acrylonitrile.

Other combinations of polyvalent metal oxides with the oxides of antimony and of tin have been shown in a very general fashion in such patents as French Pat. Nos. 2,020,512 and 2,065,317 and in British Pat. No. 1,280,073. Certain of these combinations, and particularly those of French Pat. No. 2,176,771, increase the conversion rate of propylene to acrylonitrile, but this requires relatively long contact times so that the productivity is insufficient for industrial usage.

THE INVENTION

It has been surprisingly found according to the present invention that on the occasion of a study of the activities of catalysts for the ammoxidation of olefins utilizing as a base the oxides of antimony and of tin together with one or more polyvalent metal oxides that the performances of such combinations of oxides can be appreciably improved by their association with one or more compounds of certain monovalent metals, and more particularly the alkali metals of Group I A of the periodic table of elements. Such improvement is quite marked particularly with catalysts based on the oxides of tin, antimony, tungsten, and copper that the present work has otherwise shown to be particularly interesting in themselves.

The catalysts according to the present invention can be represented by the empirical formula $$Sb_a Sn_b (Me_c)_m (A_d)_n O_e \qquad (I)$$

in which Me represents a polyvalent metal such as iron, copper, tungsten, cobalt, nickel, titanium, uranium, manganese, thorium, cerium, or aluminum; A represents a metal of Group I A of the periodic table of elements, namely, lithium, sodium, potassium, rubidium, cesium, and/or francium; $a$ is from one to ten, $b$ is from one to ten, $c$ is from 0.01 to five, and $d$ is from 0.01 to five; $m$ and $n$ are whole numbers equal to or greater than 1; and $e$ is the number of atoms of oxygen of the oxide composition obtained in combination with the metallic elements of formula (I). The value of $e$ is generally not critical and depends on the number and the nature of the oxide compounds comprising the catalyst according to the present invention.

The processes of the present invention involve ammoxidation to olefins to the corresponding unsaturated nitriles, as set forth herein.

A further advantage arising through use of the catalysts of the present invention, is that no preliminary treatment of the catalyst is required under special atmospheres, such as ammonia, hydrogen or propylene such as is described in U.S. Pat. No. 3,625,867. Moreover, it is not necessary to introduce into the mixture of reactants a saturated hydrocarbon gas, such as methane, as is described in French Pat. No. 2,151,947, or carbon monoxide or carbon dioxide as shown in French Pat. No. 2,151,946.

The catalysts according to the present invention can be prepared by a number of different methods. Thus, for example, they can be prepared by intimate mixing of the oxides, by separate precipitation or by coprecipitation beginning with salts or soluble compounds of the constituent elements, by separate or simultaneous thermal decomposition of compounds convertible to the oxides upon heating, or by a combination of these various techniques.

The alkali metal component is generally introduced during the course of preparation of the catalyst in the form of the hydroxide or in the form of a soluble or insoluble compound, such as for example, potassium nitrate, potassium carbonate, or potassium antimonate. A preferred alkali metal for use in the present catalysts is potassium.

Regardless of the means of preparation chosen to prepare the catalysts, a heat treatment at a temperature of from about 550° to about 1,000° C under an oxygen-containing atmosphere, for example, air is utilized. In certain embodiments, a temperature of from 700° to 900° C is preferred. After thermal treatment, the catalysts of formula (I) are ready to use.

They have shown themselves to be particularly useful for catalyzing ammoxidation reactions of olefins, and in particular of propylene, under the usual known operating conditions. In the case of ammoxidation of propylene, the reactants used are oxygen, ammonia, and propylene. The propylene can be mixed with paraffinic hydrocarbons such as those generally present in commercial propylene. Examples of such other hydrocarbons include ethane and propane.

In addition to other oxygen-containing mixtures, a source of oxygen for use in the processes according to the present invention can, for economic reasons, be air. The molar ratio of oxygen/propylene and of ammonia/propylene can vary over a relatively wide range of values. The molar ratio of oxygen/propylene is generally between about 0.5/1 and 3/1, and in certain preferred embodiments it is greater than 1.5/1. The molar ratio ammonia/propylene is in general between about 0.7 and 3, and in certain preferred embodiments is from about 0.9 to about 1.5.

The catalytic conversion reaction of propylene to acrylonitrile is generally effected in the presence of water vapor or of an inert diluent which can comprise from about 5 to about 40% by volume of the total volume of reactants, and in certain preferred embodiments it generally comprises from about 10% to about 25% by volume of the reactants.

The temperature of the reaction is generally maintained at from about 350° to about 520° C and is most usually between 380° and 500° C. The pressure utilized for the ammoxidation reaction can be subatmospheric or superatmospheric, and atmospheric pressures are generally preferred in the practice of the present invention.

The contact time, calculated under normal temperature and pressure, that is, 0° C at 760 mm Hg, can vary widely, for example, from about 0.5 to about 10 seconds. In certain desirable embodiments the contact time is between about 1 and about 6 seconds. Particularly useful results are obtained with contact times from about two to about four seconds, which times correspond to the requirements of industrial use.

The catalyst can be prepared in the form of pellets, rods, granules obtained by extrusion or not, or fine particles according to the type of reactor in which the catalyst will be used, and in particular according to whether the catalyst is to be used in a fixed bed reactor or in a fluidized bed reactor. The catalyst can be utilized just as it is, or it can be carried on catalyst supports of known types, such as silica and like materials.

All parts, percentages and proportions herein and ratios are by weight, unless otherwise indicated.

The following examples are given to illustrate embodiments of the invention as it is presently preferred to practice it. It will be understood that these examples are illustrative, and the invention is not to be considered as restricted thereto except as indicated in the appended claims.

EXAMPLE I

Under agitation, 4130 g of an aqueous solution of nitric acid containing 18.5% of $HNO_3$ is heated to 95° C and 438 g of antimony oxide, $Sb_2O_3$, in powder form is dispersed in the solution, whereupon 180 g of tin in powder form is added while maintaining the temperature at 97°–99° C. The suspension obtained is thereafter maintained for 15 minutes at boiling and then, under constant agitation, cooled to 40° C.

Agitation is stopped and after decantation, the supernatant liquid is removed by siphonage. The remaining solid mass is then washed under agitation for 15 minutes with cold water, and then after decantation and siphonage of the supernatant liquid, it is washed again with 4 liters of water at a temperature of 98°–100° C. After cooling to 40° C, decantation, and siphonage of the supernatant liquid, the solid mass is resuspended in 2.5 liters of water and maintained at 60° C, whereupon 43.5 g of tungsten anhydride, $WO_3$, and then 90.6 g of cupric nitrate, $Cu(NO_3)_2.3 H_2O$, are added. Gaseous ammonia is introduced into the resulting liquid until a pH value of 6.3 to 6.5 is obtained.

After cooling, decantation, and siphonage of the supernatant liquid, 2.1 g of potassium hydroxide, KOH, dissolved in the minimum quantity of water, is mixed under agitation with the so obtained slurry and immediately dried at 150° C for 16 hours. The dry powder is pelletized after the addition of 1% of graphite to serve as a lubricant. The pellets are heat treated under an air stream for 16 hours at 775° C.

The pellets of the catalyst, having dimensions of 4 mm by 5 mm, contain an atomic ratio of metals, Sb, Sn, W, Cu and K of 4/2/0.25/0.5/0.05, and 30 g of this catalyst is placed in a catalytic reactor comprising a glass U-tube with an inside diameter of 10 mm. The tube is immersed in a bath of molten nitrate maintained at 480° C. Through this catalyst is passed 18 liters/hr of a gaseous mixture with a molar composition of 6% propylene, 7% ammonia, 70% air, and 17% water. Under these conditions, 72.8% of propylene is converted to acrylonitrile, while 8.1% is transformed to oxides of carbon, $CO_2$ and CO.

Under the same conditions the same mixture of gases is treated with a catalyst which does not contain potassium, but does contain the other metallic elements antimony, tin, tungsten, and copper in the same relative atomic proportions: 4/2/0.25/0.5. It is found, as low as 440° C, that 23.2% of the propylene put into reactor is transformed to the oxides of carbon while only 61.6% propylene is converted to acrylonitrile.

EXAMPLE II

Operating under the same conditions as those of Example I and utilizing the same catalyst with an atomic ratio of Sb/Sn/W/Cu/K of 4/2/0.25/0.5/0.05, with the gaseous mixture of reactants fed at the rate of 27 liters/hr, 68% of the propylene is transformed to acrylonitrile and 11.2% to the oxides of carbon, that is, carbon dioxide and carbon monoxide. Under the same conditions utilizing a catalyst not containing potassium, but where the other metals are in the same relative proportion, only 64.5% of propylene is transformed to acrylonitrile while 19.6% is transformed to the oxides of carbon.

EXAMPLE III

A catalyst is prepared following the procedure of Example I until the introduction of the tungsten anhydride. At the same time as the tungsten anhydride is added, 64.6 g of cobalt nitrate, $Co(NO_3)_2.6 H_2O$, and 292.5 g of an aqueous solution of ferric nitrate containing 46% by weight of $Fe(NO_3)_3$ are also added. The suspension is then maintained at 60° C and its pH is adjusted to 8–8.2 by the introduction of ammonia.

After cooling, decantation, and drawing off the supernatant liquid, 2.1 g of potassium hydroxide, KOH, dissolved in the minimum of water is added and mixed with the so obtained slurry under agitation. After drying the mixture at 150° C for 16 hours, the dry powder obtained is put into the form of pellets after the addition of 1% of graphite to serve as a lubricant for the pelletizing, and the pellets are heat treated under an air current for 16 hours at 775° C.

Utilizing the same apparatus as that for Example I, 30 g of catalyst pellets with dimensions of 4 × 5 mm containing the elements Sb/Sn/Co/Fe/K in relative atomic proportions 4/2/0.25/0.25/0.75/0.05 prepared according to the process described in Example I is thermally treated at 775° C.

The bath of molten nitrate is heated to 470° C. Through the reactor containing this catalyst is passed 36 liters/hr of the gaseous mixture of same proportions as used in Example I, that is to say, 6% propylene, 7% ammonia, 70% air, and 17% of water. Under these conditions 54.8% of the propylene is converted to acrylonitrile and 15.6% is changed to carbon dioxide and carbon monoxide.

While operating under the same conditions with a catalyst which does not contain potassium, the relative proportions of the other metals being the same, 27.5% of the propylene is converted to carbon dioxide and carbon monoxide at temperatures as low as 400° C and at this temperature only 18.9% of the propylene is converted to acrylonitrile.

It will be appreciated by those skilled in the art from the present description that the catalysts and processes are quite useful for conversion of lower olefins to the corresponding nitriles and that propylene and isobutene can readily be used to provide acrylonitrile and methacrylonitrile.

What is claimed is:

1. A process for producing acrylonitrile or methacrylonitrile which comprises reacting, respectively, propylene or isobutene, ammonia, and oxygen in the presence of a catalyst to produce the corresponding nitrile, the catalyst consisting essentially of oxides of antimony and of tin in combination with one or more other polyvalent metal oxides and oxides of one or more alkali metals according to the formula $$Sb_a Sn_b (Me_c)_m (A_d)_n O_e$$

wherein Me is a polyvalent metal and is iron, copper, tungsten, cobalt, nickel, titanium, uranium, manganese, thorium, cerium, or aluminum, A is an alkali metal, $a$ is from 1 to 10, $b$ is from 1 to 10 $c$ is from 0.01 to 5, $d$ is from 0.01 to 5, $m$ and $n$ are integers and are one or more, and $e$ is the number of oxygen atoms in combination with the metallic elements, the catalyst being prepared by intimate mixing of the oxides, by separate precipitation or by coprecipitation beginning with salts or soluble compounds of the constituent elements, by separate or simultaneous thermal decomposition of compounds convertible to the oxides upon heating, or by a combination thereof and being subjected to a heat treatment at a temperature of from about 550° C to about 1000° C under an oxygen-containing gas.

2. A process according to claim 1 wherein the polyvalent metals are copper and tungsten and the monovalent metal is potassium.

3. A process according to claim 1 wherein the polyvalent metals are tungsten, cobalt, and iron, and the monovalent metal is potassium.

4. A process according to claim 1 wherein $e$ is from about 4 to about 80.

5. A process according to claim 1 wherein the catalyst is in the form of pellets, rods, granules, or fine particles.

6. A process according to claim 1 wherein the heat treatment is carried out at from 700° C to 900° C.

* * * * *

UNITED STATES PATENT AND TRADEMARK OFFICE
CERTIFICATE OF CORRECTION

PATENT NO. : 4,035,410
DATED : July 12, 1977
INVENTOR(S) : JACQUES MARION; CHRISTIAN PRALUS It is certified that error appears in the above-identified patent and that said Letters Patent are hereby corrected as shown below:

Column 2, line 2, change "to" (first instance) to --of--.

Column 4, line 46, change "Sb/Sn/Co/Fe/K" to --Sb/Sn/W/Co/Fe/K--

Column 5, line 18, after "10" (second instance) add a comma.

Signed and Sealed this

Thirteenth Day of December 1977

[SEAL]

Attest:

RUTH C. MASON
Attesting Officer

LUTRELLE F. PARKER
Acting Commissioner of Patents and Trademarks